US008937477B2

(12) United States Patent
Murayama

(10) Patent No.: US 8,937,477 B2
(45) Date of Patent: Jan. 20, 2015

(54) BIOCHEMICAL MEASURING DEVICE

(75) Inventor: Tatsuro Murayama, Tokyo (JP)

(73) Assignee: Tanita Corporation, Tokyo (JP)

( * ) Notice: Subject to any disclaimer, the term of this patent is extended or adjusted under 35 U.S.C. 154(b) by 309 days.

(21) Appl. No.: 13/424,077

(22) Filed: Mar. 19, 2012

(65) Prior Publication Data
US 2012/0293181 A1 Nov. 22, 2012

(30) Foreign Application Priority Data

May 16, 2011 (JP) ................................ 2011-109058

(51) Int. Cl.
G01N 27/32 (2006.01)
G01N 27/327 (2006.01)
(52) U.S. Cl.
CPC ................................ G01N 27/3273 (2013.01)
USPC ....................... 324/439; 204/403.01; 436/150
(58) Field of Classification Search
CPC ....................... G01N 27/3273; G01N 27/3274
USPC .......................................... 324/439; 436/150
See application file for complete search history.

(56) References Cited

U.S. PATENT DOCUMENTS

| 8,388,821 B2* | 3/2013 | Blythe et al. ............. 204/403.02 |
| 2003/0178998 A1* | 9/2003 | Ikura et al. .................... 324/448 |
| 2008/0159914 A1* | 7/2008 | Ohashi et al. ................ 422/68.1 |
| 2010/0147707 A1* | 6/2010 | Liu et al. .................... 205/790.5 |

FOREIGN PATENT DOCUMENTS

| JP | 9-297120 | | 11/1997 |
| JP | 2002071637 A | * | 3/2002 |
| JP | 2008241410 A | * | 10/2008 |

* cited by examiner

Primary Examiner — Jeff Natalini
(74) Attorney, Agent, or Firm — McDermott Will & Emery LLP

(57) ABSTRACT

The invention provides a biochemical measuring device including: a measuring unit configured to measure a base current and a peak current; a time counting unit configured to count an elapsed time from the contact of a sensor electrode to a reference solution until the start of measurement of the base current; and a control unit, wherein the control unit acquires a concentration of a specific substance using the base current value when the elapsed time is equal to or longer than a stationarizing time, and when it is shorter than the stationarizing time, acquires the concentration of the specific substance using the stationary base current value measured by the measuring unit when the elapsed time is shorter than the stationarizing time instead of the current value of the base current.

7 Claims, 6 Drawing Sheets

BIOCHEMICAL MEASURING DEVICE

BACKGROUND OF THE INVENTION

1. Field of the Invention

The present invention relates to a biochemical measuring device configured to measure a concentration of a specific substance contained in measured sample solution including electrolyte and, more specifically, to a biochemical measuring device configured to be capable of reducing a waiting time when measuring a concentration of a specific substance continuously.

2. Description of the Related Art

In the related art, a biochemical measuring device configured to measure a concentration of a specific substance contained in measured sample solution is used. As one of biochemical measuring devices, JP-A-9-397120 discloses a urine glucose meter configured to measure a specific substance contained in urine as measured sample solution, that is, a urine glucose value (glucose concentration) by a glucose sensor as a current detecting-type chemical sensor. For example, a two-electrode type glucose sensor includes a pair of conductive electrodes (a working electrode and a counter electrode) arranged on an insulative substrate, and an enzyme (glucose oxidase) film is formed on the conductive electrodes.

The glucose sensor is subject to chemical reaction in the measured sample solution as follows. By the action of the glucose oxidase, glucose in the measured sample solution is oxidized, oxygen is reduced to hydrogen peroxide, so that gluconolactone and hydrogen peroxide are generated. At this time, by an application of a voltage to the electrodes (the working electrode and the counter electrode), oxidizing reaction of the hydrogen peroxide is generated on the working electrode, thereby generating electrons and an oxidation current flows from the working electrode to the counter electrode, and the flowed oxidation current is measured as an oxidation current value. Since the amount of generation of the hydrogen peroxide is proportional to the amount of glucose, if the oxidation current value of the hydrogen peroxide is known, the concentration of urine glucose (glucose) can be measured.

Therefore, when measuring the urine glucose value using the urine glucose meter, the urine glucose concentration is measured on the basis of a difference between a base current value of a base current flowed by an application of a constant potential to a point between both electrodes (the working electrode and the counter electrode) in a state of being immersed in preservative solution which does not contain the urine glucose and a peak current value of an oxidation current flowing between the both electrodes by the application of a constant potential between the both electrodes (the working electrode and the counter electrode) in the measured sample solution.

However when a predetermined potential is applied to a point between the pair of electrodes, a charge is accumulated on a surfaces of the respective electrodes by the formation of an electric bilayer. In order to eliminate the influence of the electronic bilayer, when the urine glucose value is measured continuously by the urine glucose meter, it is required to wait for a waiting time from the termination of previous measurement and subsequent immersion of electrodes of the urine glucose meter in the preservative solution until the restoration of the base current value to a stationary current value which indicates a urine glucose concentration of zero (for example, 3 minutes) has elapsed before restarting the measurement with the urine glucose meter. Consequently, when there are a plurality of types of measured sample solution to be measured or the first measurement of the urine glucose value is failed, it is required to wait until the elapse of the waiting time before restarting the measurement.

SUMMARY OF THE INVENTION

Accordingly, it is an object of the invention to provide a biochemical measuring device in which a waiting time from the termination of a previous measurement until becoming ready to execute the next measurement can be reduced.

In order to solve the above-described problem, there is provided a biochemical measuring device configured to measure a concentration of a specific substance in measured sample solution containing electrolyte including: a measuring unit configured to measure a base current generated by applying a predetermined potential to a sensor electrode which is in contact with reference solution and to measure a peak current generated by applying the predetermined potential to the sensor electrode which is in contact with the measured sample solution; a time counting unit configured to count an elapsed time from the contact of the sensor electrode to the reference solution until the start of measurement of the base current; and a control unit configured to acquire a concentration of the specific substance on the basis of a current value of the base current and a current value of the peak current, wherein when the elapsed time is equal to or longer than a stationarizing time required until the current value of the base current is returned to a stationary base current value which indicates that the specific substance has a reference concentration, the control unit acquires the concentration of the specific substance using the current value of the base current, and when the elapsed time is shorter than the stationarizing time, the control unit acquires the concentration of the specific substance using the stationary base current value measured by the measuring unit when the elapsed time is equal to or longer than the stationarizing time instead of the current value of the base current.

Preferably, when the elapsed time is shorter than the stationarizing time, the control unit acquires the concentration of the specific substance using latest data from among the stationary base current values measured by the measuring unit when the elapsed time is equal to or longer than the stationarizing time instead of the current value of the base current.

Preferably, the base current measured by the measuring unit includes a first base current generated by an application of a predetermined potential to the sensor electrode which is in contact with the reference solution before a first measuring process and a second base current generated by an application of a predetermined potential to the sensor electrode in contact with the reference solution after the first measuring process, the peak current measured by the measuring unit includes a first peak current generated by an application of the predetermined potential to the sensor electrode which is in contact with the measured sample solution in the first measuring process and a second peak current generated by an application of the predetermined potential to the sensor electrode in contact with the measured sample solution in a second measuring process to be performed after the first measuring process, the elapsed time counted by the counting unit is an elapsed time from the contact of the sensor electrode to the reference solution after the first measuring process until the start of the measurement of the second base current, when the elapsed time is equal to or longer than a stationarizing time required until the current value of the second base current is returned to the first base current value, the control unit acquires the concentration of the specific substance of the measured sample solution in the second measuring process using the current value of the second base current and the current value of the second peak current, and when the elapsed time is shorter than the stationarizing time, the control unit acquires the concentration of the specific substance of the measured sample solution in the second measuring process using the current value of the first base current and the current value of the second peak current.

Preferably, the biochemical measuring device of the invention further includes a notifying unit configured to remind a user when the current value of the second peak current is lower than the current value of the second base current measured by the measuring unit when the elapsed time is shorter than the stationarizing time.

Preferably, the sensor electrode is provided at one end side of a sensor holder and the other end side of the sensor holder is coupled to a main body via a hinge portion, so that the sensor holder is configured to be rotatable between a first state in which the sensor holder is expanded from the main body and a second state in which the sensor holder is folded with respect to the main body, and the time counting unit is configured to start counting of the elapsed time by considering that the sensor electrode is brought into contact with the reference solution when the sensor holder is switched from the first state to the second state.

Preferably, the measured sample solution is urine, and the specific substance is urine glucose.

Advantages of the Invention

The invention is configured in such a manner that when the elapsed time from when the concentration of the specific substance of the previous measured sample solution is measured ends before the elapse of the stationarizing time, the acquisition is achieved when the stationarizing time is elapsed and the concentration of the specific substance is measured on the basis of the stationary base current value which indicates that the concentrate of the specific substance is zero. Therefore, the influence of the electric bilayer on the base current value to be measured may be eliminated. Consequently, according to the biochemical measuring device of the invention, accurate detection of the concentration of the specific substance is achieved even before the elapse of the stationarizing time.

DESCRIPTION OF PREFERRED EMBODIMENT

[Urine Glucose Meter]

Figure 1:
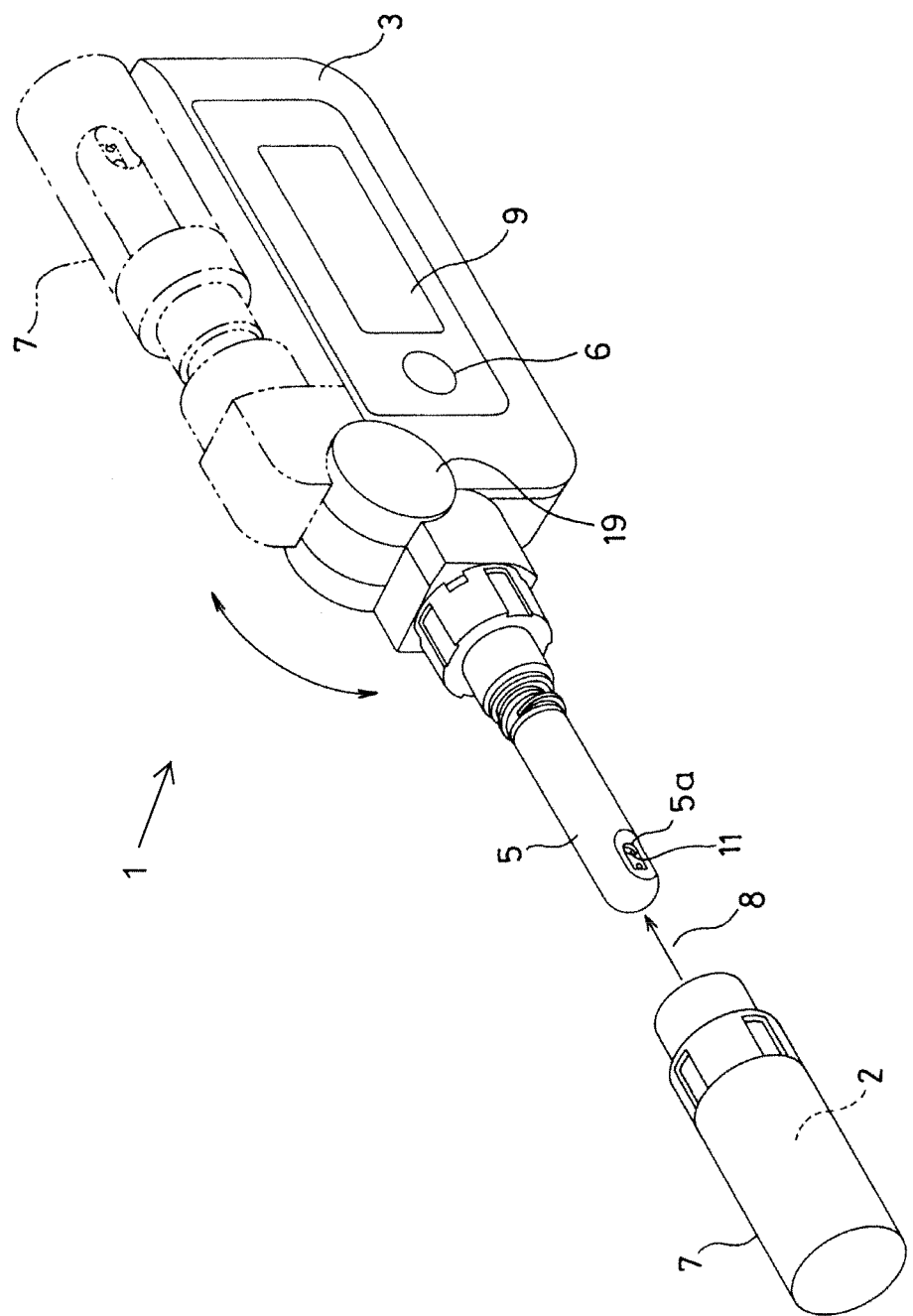
FIG. 1 is a perspective view diagrammatically showing a general configuration of a urine glucose meter according to an embodiment of the invention.

Referring now to the drawings, an embodiment of a urine glucose meter to which a biochemical measuring device according to the invention is applied will be described. FIG. 1 is a perspective view schematically showing a general configuration of a urine glucose meter 1 according to an embodiment of the invention, and FIG. 2 is a block diagram showing an electric configuration of the urine glucose meter 1 shown in FIG. 1.

Figure 2:
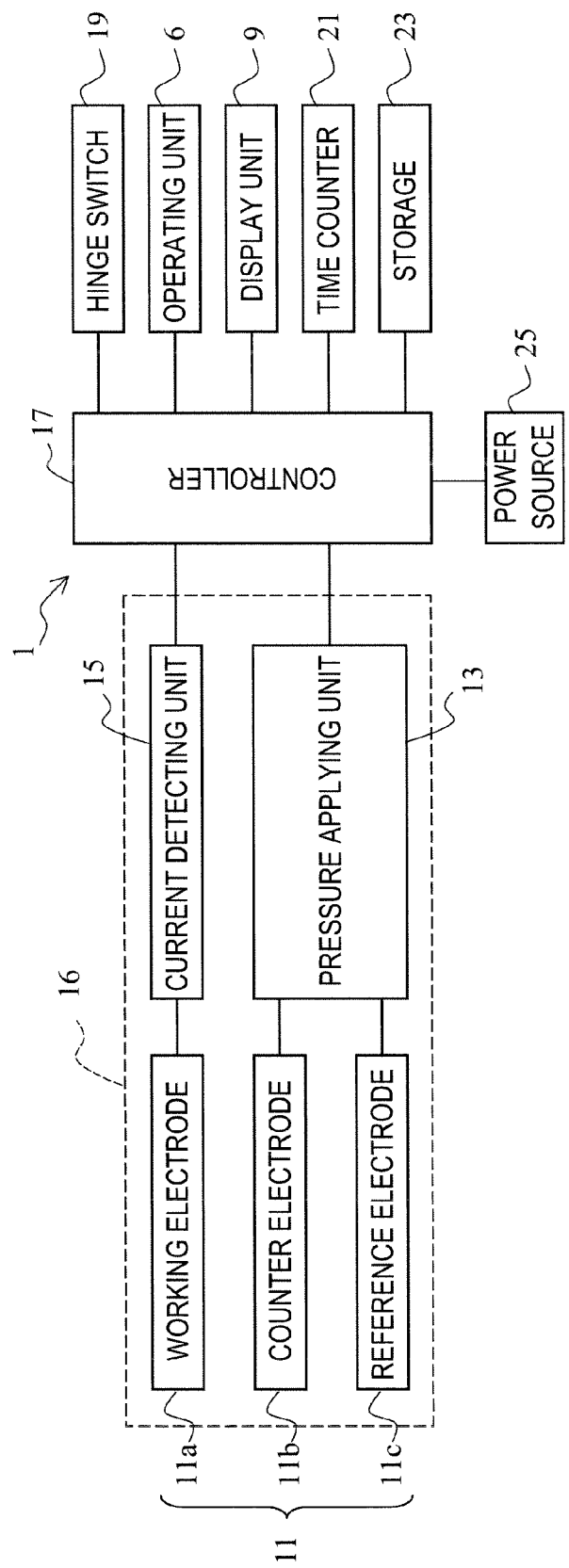
FIG. 2 is a block diagram showing an electrical configuration of the urine glucose meter shown in FIG. 1.

As shown in FIG. 1 and FIG. 2, the urine glucose meter 1 mainly includes a glucose sensor 11 as a measuring unit, a time counter 21 as a time counting unit, and a controller 17 as a control unit. The glucose sensor 11 includes at least a working electrode (first electrode) 11a and a counter electrode (second electrode) 11b as sensor electrodes, and is configured to measure a base current generated by an application of a predetermined potential in a state in which the working electrode 11a and the counter electrode 11b are in contact with (or immersed into) a preservative solution 2, and measures a peak current generated by an application of a predetermined potential in a state in which the working electrode 11a and the counter electrode 11b are in contact with (or immersed into) urine as measured sample solution. The time counter 21 measures an elapsed time from a contact of the working electrode 11a and the counter electrode 11b with the preservative solution 2 until the base current is measured, and a measuring time (for example, 6 seconds) from a contact of the glucose sensor 11 with the measured sample solution until a peak current for a certain period is measured. The controller 17 acquires a concentration of urine glucose on the basis of a base current value of the base current and a peak current value of the peak current acquired by the glucose sensor 11.

The urine glucose meter 1 has a configuration in such a manner that when the elapsed time is equal to or longer than the stationarizing time required for the current value of the base current to return to a stationary base current value which indicates that the urine glucose (specific substance) has a reference concentration (for example, the concentration is zero), the controller 17 (control unit) acquires the concentration of the specific substance using the current value of the base current and, when the elapsed time is shorter than the stationarizing time, the controller 17 acquires the concentration of the specific substance using the stationary base current value measured by the glucose sensor 11 (measuring unit) when the elapsed time is equal to or longer than the stationarizing time instead of the current value of the base current.

In addition, respective components of the urine glucose meter 1 will be described in detail. As shown in FIG. 1, the urine glucose meter 1 includes a urine meter body 3, a sensor holder 5, an operating unit 6, and a cap 7. The urine meter body 3 is a housing having the controller 17, the time counter 21 and the like integrated therein, and a display unit (LCD (Solution Crystal Display)) 9 which corresponds to a display unit (notifying unit) which displays various items of information to users at a substantially center of the urine meter body 3. The display 9 displays urine glucose values (urine glucose concentration), date and time of measurement, and so on. The operating unit 6 is used mainly for an operation for causing the display 9 to display the measurement values in the past, an operation for switching the mode to a calibration mode or a communication mode, and the like.

When the measurement is performed with the urine glucose meter 1, the sensor holder 5 is brought into a state of being expanded (the state shown by a solid line in FIG. 1). One end of the sensor holder 5 is mounted so as to be rotatable in the direction indicated by an arrow in FIG. 1 with respect to the urine meter body 3. The other end of the sensor holder 5 is provided with the glucose sensor 11, and is provided with an opening 5a so that the preservative solution 2 or urine as the measured sample solution can come into contact with the glucose sensor 11 from the outside.

When storing the urine glucose meter 1, a distal end portion of the sensor holder 5 is covered with the cap 7 as indicated by an arrow 8. The urine glucose meter 1 is stored in a state in which the sensor holder 5 with the cap 7 fitted thereon in the expanded state is rotated toward the urine meter body 3 (the state indicated by a double-dashed chain line in FIG. 1) and is folded on the upper surface side of the urine meter body 3. The preservative solution (reference solution) 2 for returning the base current value of the glucose sensor 11 to a reference value is filled in the interior of the cap 7. The preservative solution 2 in the cap 7 is preferably preservative solution in which the concentration of the specific substance (urine glucose) is zero, and the state of the glucose sensor 11 is kept always in an optimal state. However, the reference solution which is capable of providing a reference concentration which can be a reference when measuring the concentration is applicable.

(Electrical Configuration of Urine Glucose Meter 1)

Referring now to FIG. 2, an electrical configuration of the urine glucose meter 1 will be described. Electrically connected to the controller 17 are the glucose sensor 11, a voltage applying unit 13, a current detecting unit 15, the controller 17, a hinge switch 19, the operating unit 6, the display 9, the time counter 21, a storage 23, and a power source 25.

The glucose sensor 11 includes three-electrode system in which the working electrode 11a, the counter electrode 11b, and a reference electrode 11c formed of a conductive material are arranged on an insulative substrate. The working electrode 11a is covered with an enzyme film formed of glucose oxidase. The voltage applying unit 13 and the current detecting unit 15 are electrically connected to the glucose sensor 11. In other words, the voltage applying unit 13, the current detecting unit 15, and the glucose sensor 11, and also a lead wire that connects these members constitute a potentiostat 16 which corresponds to a measuring unit, and is configured to detect a current value of a current flowing from, the working electrode 11a to the counter electrode 11b while controlling the potential of the counter electrode 11b so as to maintain the potential between the working electrode 11a and the reference electrode 11c to be constant at any time by the signal from the controller 17. Although the glucose sensor of a three-electrode system is used in this embodiment, a glucose sensor of a two-electrode system which does not have the reference electrode 11c (third electrode) may also be used.

The storage 23 includes, for example, a RAM (Random Access Memory) or a ROM (Read Only Memory), and the like, and includes a program which operates the urine glucose meter 1, data detected by the glucose sensor 11 stored therein, and the like.

Switching of the urine glucose meter 1 between the measurable state and the waiting state in this embodiment is performed by the hinge switch (hinge portion) 19. When the sensor holder 5 is brought into a state in which the sensor holder 5 is expanded from the urine meter body 3 (the state shown by the solid line in FIG. 1, the first state), the device is brought into a measurable state in which a measuring process of the concentration of a specific substance contained in the measured sample solution can be performed, and when the cap 7 is mounted and the sensor holder 5 is brought into a state of being folded (the second state, the state shown by the double-dashed chain line in FIG. 1), the measurable state is released, and the urine glucose meter 1 is brought into the waiting state. Also in the waiting state, it is preferable to configure the glucose sensor 11 immersed in the preservative solution 2 in the cap 7 to be applied with a predetermined potential. In this configuration, the state of the urine glucose meter 1 may be switched from the first state to the second state without waiting for a period from the initiation of the application of the predetermined potential until the stabilization of the base current, so that the device may be used immediately after the cap 7 has removed from the sensor holder 5, whereby the convenience for the user is improved.

The time counter 21 as a time counting unit which counts the time is used for counting the time from when the glucose sensor 11 is immersed in the preservative solution 2 in the cap 7 until the base current of the measured sample solution is detected by the current detecting unit 15. When the sensor holder 5 is folded, the urine glucose meter 1 is brought into a waiting state by the hinge switch 19, and the count of the elapsed time by the time counter 21 is started. Also, the time counter 21 measures a measuring time from a contact of the glucose sensor 11 with the measured sample solution until a peak current for a certain period is measured.

This embodiment is configured to count the elapsed time and perform the measuring process under the condition that the timing when the glucose sensor 11 is immersed in the preservative solution 2 and the timing when the hinge switch 19 is folded are performed in the same timing. In other words, the elapsed time from when the glucose sensor 11 is immersed in the preservative solution 2 until the sensor holder 5 is expanded and the base current value of the measured sample solution is measured with the current detecting unit 15 is acquired by counting a period from when the sensor holder 5 is folded (that is, brought into the second state) until the sensor holder 5 is expanded and the base current of the measured sample solution is measured by the current detecting unit 15.

The urine glucose meter 1 of this embodiment has a configuration in which the measurable state and the waiting state of the urine glucose meter 1 is switched by rotating the sensor holder 5. However, a configuration to switch the same by the operation of the operating unit 6 is also possible and a configuration in which a solution crystal having a touch panel function is used for the display 9 and the switching is achieved by the operation thereof is also applicable.

(Flow of Method of Measuring Urine Glucose)

Figure 3:
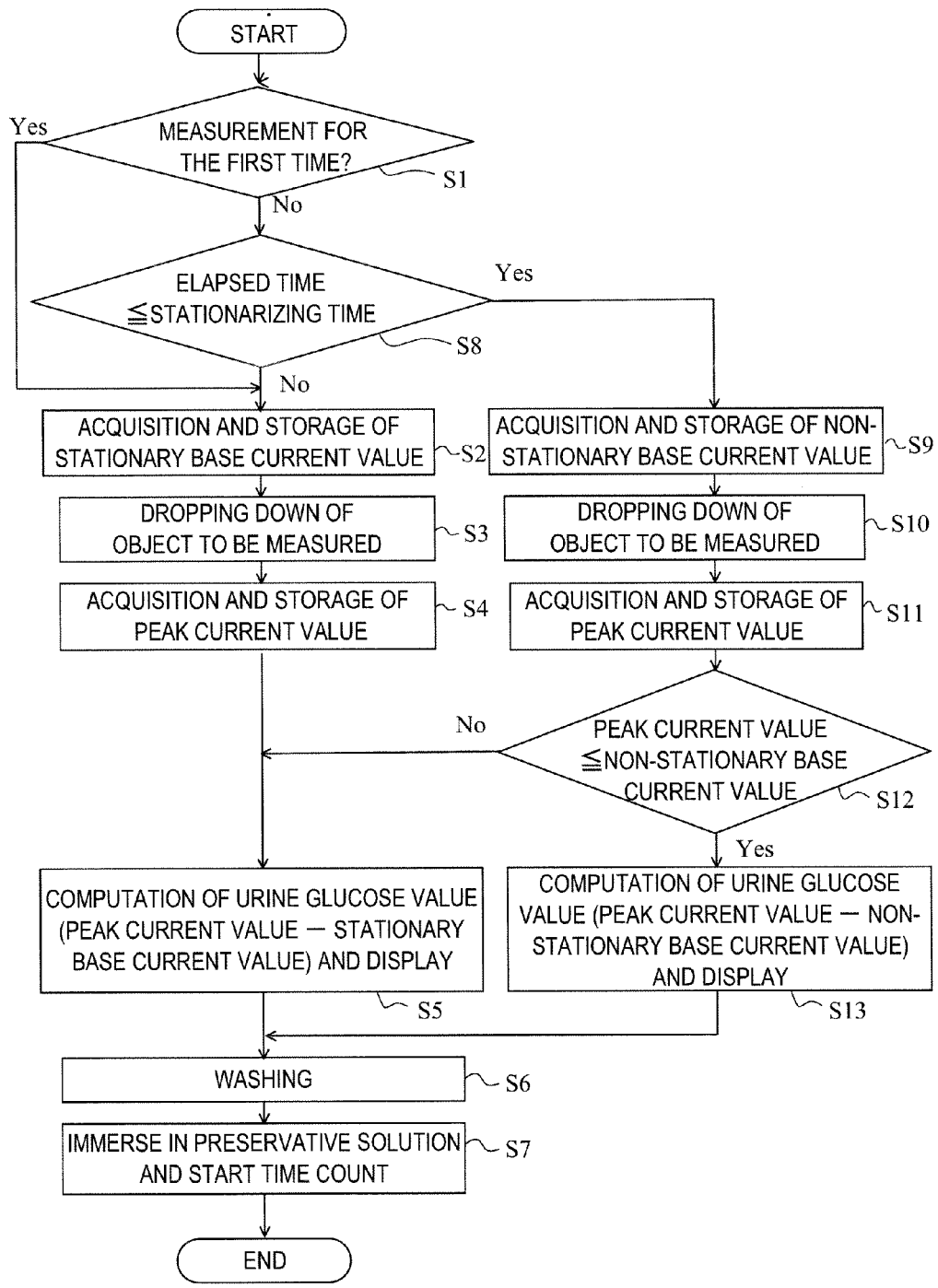
FIG. 3 is a flowchart showing a method of measurement using the urine glucose meter shown in FIG. 1.
Figure 4:
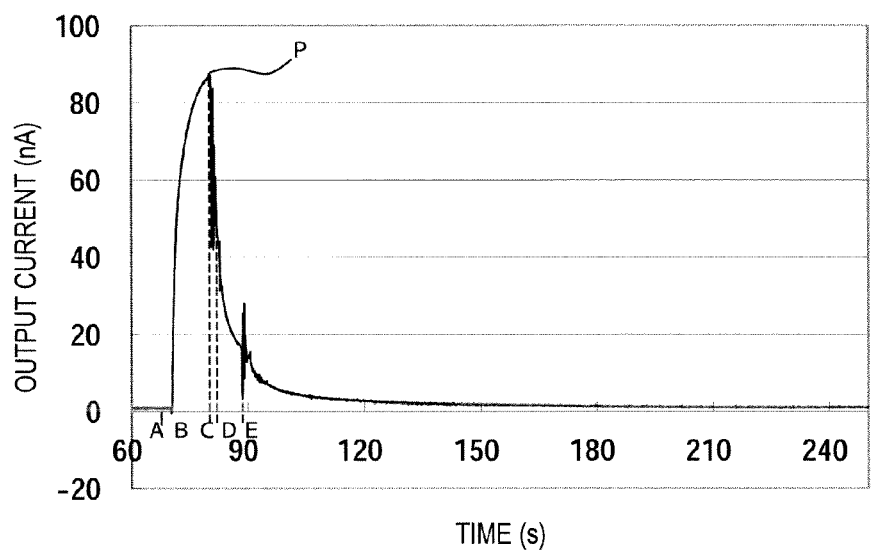
FIG. 4 is a graph showing a change of an output current with time when a urine glucose value is measured with the urine glucose meter shown in FIG. 1.
Figure 5:
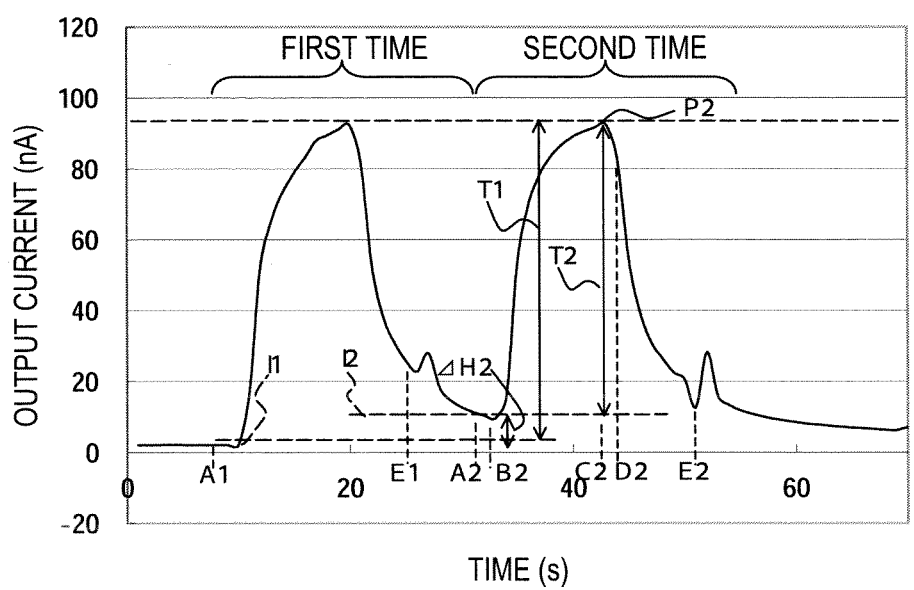
FIG. 5 is a graph showing a change of an output current with time when the urine glucose value is measured in an elapsed time shorter than a stationarizing time with the urine glucose meter shown in FIG. 1.
Figure 6:
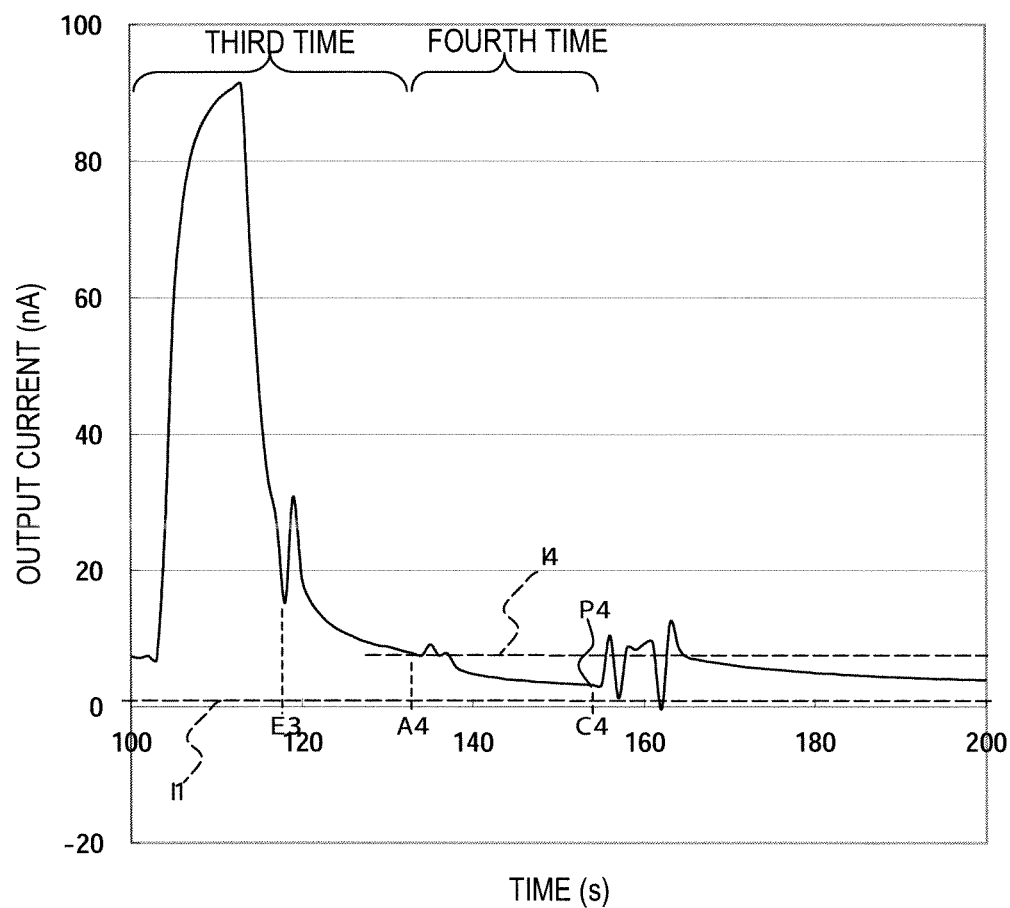
FIG. 6 is a graph showing a change of an output current with time when the urine glucose value of urine having a relatively low degree of urine glucose is measured with the urine glucose meter shown in FIG. 1.

A flow of a method of measurement of the urine glucose using the urine glucose meter 1 will be described with reference mainly to FIG. 3 to FIG. 6. FIG. 3 is a flowchart showing a method of measurement using the urine glucose meter 1 shown in FIG. 1; FIG. 4 is a graph showing a change with time of an output current when the urine glucose value is measured with the urine glucose meter 1 shown in FIG. 1; FIG. 5 is a graph showing a change with time of an output current when the urine glucose value is measured by the urine glucose meter 1 shown in FIG. 1 (measurements for the first and the second times); FIG. 6 is a graph showing a change with time of the output current when the urine glucose value is measured by the urine glucose meter 1 (measurements on the third and the fourth times) shown in FIG. 1. The vertical axis of the graph in FIG. 4 to FIG. 6 shows an output current value (nA) detected by the current detecting unit 15, and the lateral axis shows the time (seconds). In the measuring process for the second time in the graph in FIG. 5, the urine glucose value is measured in an elapsed time shorter than the stationarizing time. In the measuring process for the fourth time the graph in FIG. 6, urine having a relatively low degree of urine glucose is measured.

In order to start the measurement with the urine glucose meter 1, the sensor holder 5 is expanded as indicated by the solid line in FIG. 1, the urine glucose meter 1 is switched by the hinge switch 19 to the measurable state, and whether or not it is the initial measurement (the first measuring process) to be performed using the urine glucose meter 1 is recognized (Step S1). For example, whether or not there is a base current value or the like already acquired and stored in the storage 23 is recognized by the controller 17. When the urine glucose meter 1 is used for the first time this time, since there is no base current value stored in the storage 23, it is determined that the measurement is the measurement for the first time (Yes, in Step S1) and the procedure goes to the next Step S2.

Subsequently, in a state in which the cap 7 is mounted, that is, in a state in which the glucose sensor 11 is immersed in the preservative solution 2, the voltage applying unit 13 applies a constant potential to a point between the working electrode 11a and the counter electrode 11b, and the current value of the current flowing from the working electrode 11a to the counter electrode 11b in the waiting state is acquired by the current detecting unit 15 and stored in the storage 23 (Step S2). The current value acquired at this time is a stationary base current value which indicates that the urine glucose concentration in the urine under the measuring circumstances of this time is zero, for example. This stationary base current value is stored as data (a current value of the first base current) obtained in the measuring process (first measuring process) for the first time. The stationary base current value will further be described relating to the measuring process for the second time described later.

Subsequently, after the cap 7 has removed from the sensor holder 5 by the user, urine is dropped down onto the glucose sensor 11 via the opening 5a of the urine glucose meter 1 (Step S3). The current value of the output current flowing from the working electrode 11a to the counter electrode 11b is acquired during a predetermined period by the current detecting unit 15, and a maximum value P from among the acquired current values is stored in the storage 23 as the peak current value (Step S4). The peak current value is stored as data acquired in the measuring process for the first time (the current value of the first peak current).

Then, the controller 17 computes a urine glucose value on the basis of the difference between the stationary base current value (the current value of the first base current) acquired in Step S2, and the peak current value acquired in Step S4 (the current value of the first peak current), and causes the urine glucose value to be displayed on the display 9 (Step S5). Subsequently, the glucose sensor 11 is washed by predetermined washing solution (Step S6), is covered with the cap 7, and is immersed in the preservative solution 2 (Step S7). Furthermore, when the user rotates and folds the sensor holder 5, the urine glucose meter 1 is brought into a waiting state by the hinge switch 19. Simultaneously, at the timing when the sensor holder 5 is folded, the count of the elapsed time by the time counter 21 is started (Step S7), and the measuring process (the first measuring process) is terminated. Needless to say, when the urine glucose meter 1 is kept in the waiting state, the time counter 21 is operated by a waiting power.

Subsequently, the measuring process from the second time onward will be described. In the same manner as the measuring process for the first time, in order to start the measurement with the urine glucose meter 1, the sensor holder 5 is expanded as indicated by the solid line in FIG. 1, the urine glucose meter 1 is switched by the hinge switch 19 to the measurable state, and whether or not the initial measurement to be performed using the urine glucose meter 1 is recognized (Step S1). At this time, since the stationary base current value acquired in the measuring process for the first time (the first measuring process) is stored in the storage 23, it is determined that the measurement is not the first measurement (No, in Step S1), and the procedure moves to Step S8. Then, whether or not the elapsed time from when the glucose sensor 11 is immersed in the preservative solution 2 is shorter than the stationarizing time is recognized by the controller 17 on the basis of the signal from the time counter 21 (Step S8).

Referring now to FIG. 4, the base current value and the stationarizing time will be described. In FIG. 4, a time point A is a timing when the stationary base current value is measured (Step S2 in FIG. 3), a time point B is a timing when urine is dropped down (Step S3 in a time point C is a timing when the peak current value is reached (Step S4 in FIG. 3), respectively.

In a chemical electric sensor such as the glucose sensor 11 integrated in the urine glucose meter 1, an electric bilayer is formed on an interface where electrolytic solution such as urine and electrode come into contact. By the influence of the electric bilayer described above, charge is accumulated in the electrode. Therefore, a stationarizing time according to the sensor characteristics (the predetermined period from a time point E) is required until the glucose sensor 11 is washed after the measurement (a time point D in FIG. 4, Step S6 in FIG. 3), and is immersed in the preservative solution 2 (the time point E in FIG. 4, Step S7 in FIG. 3), until the glucose sensor 11 returns to the stationary state, that to a state in which the base current value showing that the urine does not contain the urine glucose is zero (stable state).

For example, when the measurement for the first time is performed on urine having a certain urine glucose concentration using the urine glucose meter 1, the stationarizing time from when the glucose sensor 11 is immersed in the preservative solution 2 (the time point E, Step S7 in FIG. 3) until when the stable state is restored (that is, the period required until the measurement for the second time is enabled continuously) is approximately 180 seconds as shown in FIG. 4.

When the elapsed time from when the glucose sensor 11 is immersed in the preservative solution 2 (Step S7) in the measuring process for the first time (the first measuring process) is recognized as being equal to or longer than the stationarizing time (No, in Step S8), the stationary base current value indicating that the urine glucose concentration is zero can be re-acquired accurately, and therefore the procedure goes to Step S2. Subsequently, in the same manner as the measurement for the first time, when urine is dropped down on the glucose sensor 11 by the user of the urine glucose meter 1 (Step S3), the peak current value is acquired and is stored in the storage 23 (Step S4). The data on the peak current value is stored as data (the current value of the second peak current) obtained in the measuring process for the second time (the second measuring process).

Subsequently, the urine glucose concentration is computed by the controller 17 on the basis of the stationary base current value (current value of the second base current) and the peak current value (the current value of the second peak current) acquired in the measuring process for the second time, and is displayed on the display 9 (Step S5).

In contrast, when the elapsed time from when the time count is started in Step S7 of the measuring process for the first time is recognized to be shorter than the stationarizing time (Yes, in Step S8), the procedure goes to Step S9. Such a state is shown in the measuring process for the second time in FIG. 5 for example. In other words, it is a case where the measuring process for the second time (the second measuring process) is started after the measurement for the first time (the first measuring process) before the stationary base current value (a broken line I1 in FIG. 5) is returned from when the glucose sensor 11 is immersed in the preservative solution 2 (a time point E1 in FIG. 5).

In the measuring process for the second time shown in FIG. 5, in Step S9, a base current value in a state in which the current value of the current flowing from the working electrode 11a to the counter electrode 11b is not returned to a stationary state (I1) (for example, a time point A2 in FIG. 5), that is, a non-stationary base current value (I2) is obtained, and is stored in the storage 23 as a base current value for the second time (the current value of the second base current).

Subsequently, urine is dropped down on the glucose sensor 11 by the user (Step S10 in FIG. 3, a time point B2 in FIG. 5), the current value of the current flowing from the working electrode 11a to the counter electrode 11b is acquired during the predetermined period by the current detecting unit 15, a peak current value P2 as a highest value from among the acquired output current data is stored in the storage 23 as measurement data for the second time (the current value of the second peak current) (Step S11 in FIG. 3, a time point C2 in FIG. 5). Subsequently, whether or not the peak current value P2 acquired in Step S11 is equal to or lower than the non-stationary base current value acquired in Step S9 (the current value of the second base current) is recognized (Step S12 in FIG. 3).

If it is determined that the peak current value P2 acquired in the measuring process for the second time is not equal to or lower than the non-stationary base current value acquired for the second time by the controller 17 (No, in Step S12 in FIG. 3), the procedure goes to Step S5. In the measuring process for the second time, in Step S10, the non-stationary base current value I2 is acquired in the elapsed time shorter than the stationarizing time. However, computation is performed by using the stationary base current value acquired in the measurement for the first time (the current value of the first base current) I1 (Step S2 in FIG. 3) instead of using the non-stationary base current value I2 in the computation of the urine glucose value of this time (Step S5 in FIG. 3).

Since it is the measuring process for the second time at this time, the stationary base current value I1 acquired in the measuring process for the first time is used. However, when the measuring process has already executed for the plurality of times and the stationary base current values for the plurality of times have been stored in the storage 23, latest data (latest stationary base current value) from among these data may be used.

Here, referring now to FIG. 5, the reason why the non-stationary base current value is not used when computing the urine glucose value when the peak current value P2 is not equal to or lower than the non-stationary base current value acquired for the second time will be described. In FIG. 5, the measuring process for the second time (the second measuring process) is started before the stationarizing time is elapsed after the glucose sensor 11 is immersed in the preservative solution 2 (the time point E1) in the measuring process for the first time (the first measuring process), and the non-stationary base current value (the current value of the second base current) I2 is acquired (the time point A2). The urine glucose meter 1 used in FIG. 4 is used in both of the measuring processes in FIG. 5 and in FIG. 6 described later. Therefore, as long as the environment of usage is the same, the urine glucose meter 1 indicates the same stationarizing time and the stationary base current value.

As shown in FIG. 5, the base current value (a broken line I2, the time point A2) measured in the measurement for the second time indicates a higher value than the stationary base current value for the first time (a broken line I1, time point A1). Therefore, when the urine glucose value is computed on the basis of the base current value for the second time, that is, the non-stationary base current value I2 and the peak current value P2 for the second time, the urine glucose value is expressed by P2-I2 (T2). However, since the original stationarizing base current value of the urine glucose meter 1 is as indicated by the I1 (broken line), the difference in current value corresponding to the urine glucose value should be P2-I1 in precisely speaking (T1). Therefore, the urine glucose value computed on the basis of the non-stationary base current value I2 obtained by the measurement for the second time has an error of ΔH2.

In order to prevent the occurrence of the error of ΔH2, in a case where the urine glucose measuring process is continuously performed by a plurality of times, if the measuring process is started before the stationarizing time has elapsed from when the glucose sensor 11 is immersed in the preservative solution 2, the data of the stationary base current value acquired in the measuring process performed already is used, and the urine glucose value is computed using especially the latest stationary base current value (in the case of FIG. 5, the latest stationary base current value I1). The reason why the latest stationary base current value is used is for eliminating the measurement error caused by the environment of measurement by using the stationary base current value obtained at a time point temporarily close to the time point when the peak current value is measured.

Subsequently, referring to FIG. 6, the measuring process in a case where the measuring process is started at intervals shorter than the stationarizing time, and a case where the peak current value (a time point C4 in FIG. 6) becomes equal to or lower than an acquired non-stationary base current value I4 (a time point A4 in FIG. 6) will be described. FIG. 6 shows a change with time of an output current when being measured continuously as shown in a graph in FIG. 5, and results obtained by the measurements for the third time and the fourth time.

The measuring process for the fourth time is started (the time point A4 in FIG. 6) before the stationarizing time is elapsed after the glucose sensor 11 is immersed in the preservative solution 2 (a time point E3 in FIG. 6) in the measuring process for the third time, and the non-stationary base current value I4 is acquired (the time point A4). The inventors devoted themselves to study, and found that the error might occur in the peak current value when a peak current value P4 (the time point C4) is measured before the glucose sensor 11 is returned to the stable state, especially when urine having a relatively low urine glucose concentration is measured. In contrast, when the peak current value (P2) is larger than the non-stationary base current value (I2) as shown in FIG. 5, the peak current value (P2) to be measured is obtained at a sufficient accuracy. Therefore, when the peak current value P4 measured at the time point C4 in FIG. 6 is equal to or lower than the non-stationary base current value I4 measured at the time point A4, this circumstance is notified to the user of the urine glucose meter 1.

As described above, when the peak current value P4 is recognized to be equal to or lower than the non-stationary base current value (I4 in FIG. 6) (Yes, in Step S12), the fact that there is a fear that an error might be occurred in the peak current value P4 itself is notified to the user by the notifying unit of the urine glucose meter 1. More specifically, in Step S13, a notification indicating to be equal to or lower than the urine glucose value obtained by subtracting the stationary base current value I1 from the peak current value P4 acquired in the fourth measurement (for example, "≤3.9 mg/dL") is displayed on the display 9. In addition to such a display, character strings such as "error", "re-measurement required" and the like which invite the user's attention may be displayed and, furthermore, the invention is not limited thereto, and means such as a buzzer or a speaker for a voice announcement may also be applicable as long as it is a notifying unit configured to invite the user's attention.

On the other hand, in Step S12, when the peak current value P2 is not equal to or lower than the non-stationary base current value I2 (that is, the peak current value (P2 in FIG. 5) is larger than the non-stationary base current value (I2 in FIG. 5) as in the case of the measurement for the second time shown in FIG. 5, the procedure goes to Step S5. In Step S5, the urine glucose value is computed and is displayed on the display 9 on the basis of the latest stationary base current value (the current value of the first base current) I1 (obtained in the measuring process for the first time in the case of the graph shown in FIG. 5) and the peak current value (the current value of the second peak current) P2 obtained in the measuring process for the second time.

After Step S13 or Step S5 which displays the urine glucose value, a series of the measuring processes is terminated via the washing of the glucose sensor 11 (step S6), the immersion of the glucose sensor 11 into the preservative solution 2, and the start of time counting (Step S7) as described above.

In this embodiment, although the sensor which employs glucose oxidase as enzyme and is configured to detect glucose is used, the invention is not limited thereto. For example, a sensor which uses lactate oxidase, alcohol oxidase, cholesterol oxidase, pyruvate oxidase, amino acid oxidase, ascorbic acid oxidase or the like may be employed in order to detect the concentration of the organic substance such as lactic acid, alcohol, cholesterol, pyruvic acid, amino acid, ascorbic acid, and the like.

Although the device in this embodiment is configured in such a manner that the time counting by the time counter 21 is started at a timing when the urine glucose meter 1 is switched to the waiting state by the hinge switch 19, a configuration in which a switch is provided on the sensor holder 5 and, if the cap is mounted on the sensor holder 5, the time counting by the time counter 21 is started by the switch is also applicable. In other words, the invention is achieved as long as the glucose sensor 11 has a configuration in which the elapsed time from when the glucose sensor 11 comes into contact with the preservative solution 2 until the base current value is measured for the next time can be counted.

The invention may be embodied in various modes without departing the essential characteristics. Therefore, needless to say, the embodiment described above is given only for description and does not limit the invention.

What is claimed is:

1. A biochemical measuring device configured to measure a concentration of a specific substance in a measured sample solution containing electrolyte, the biochemical measuring device comprising:
   a measuring unit configured to obtain a base current value that is generated by applying a predetermined potential to a sensor electrode when the sensor electrode is in contact with a reference solution and a peak current value that is generated by applying the predetermined potential to the sensor electrode when the sensor electrode is in contact with the measured sample solution, and to measure the concentration of the specific substance based on a stationary base current value, which represents that the concentration of the specific substance is zero, and the peak current value; and
   a time counting unit configured to count an elapsed time from a time when the sensor electrode contacts the reference solution, where the biochemical measuring device is in a waiting state, until a time when the sensor electrode contacts the measured sample solution, where the biochemical measuring device is in a measurable state,
   wherein, if a measurement of the concentration of the specific substance is conducted when the elapsed time counted by the time counting unit is shorter than a stabilization time, the measuring units uses a past base current value as the stationary base current value instead of a latest base current value which is obtained in the measurement of the concentration of the specific substance, the stabilization time being a time required for a current value in measuring the base current value to return to a level of the stationary base current value after a previous measurement is conducted.

2. The biochemical measuring device according to claim 1, wherein, when the elapsed time is equal or longer than the stabilization time, the measuring unit measures the concentration of the specific substance by using the latest base current value as the stationary base current value.

3. The biochemical measuring device according to claim 1, wherein the past base current value is a latest base current value used in a previous measurement which is conducted just before the measurement.

4. The biochemical measuring device according to claim 1, further comprising:
   a main body; and
   a sensor holder having a first end and a second end, wherein:
   the sensor electrode is provided at the first end of the sensor holder,
   the second end of the sensor holder is coupled to the main body via a hinge portion, so that the sensor holder is rotatable between a first state in which the sensor holder is expanded from the main body and a second state in which the sensor holder is folded with respect to the main body, and
   the time counting unit is configured to start counting of the elapsed time when the sensor holder is switched from the first state to the second state as a time that the sensor electrode is brought into contact with the reference solution.

5. The biochemical measuring device according to claim 1, wherein the measuring unit is configured to measure urine glucose in urine as the specific substance and measured sample solution, respectively.

6. A biochemical measuring device configured to measure a concentration of a specific substance in a measured sample solution containing electrolyte comprising:
   a measuring unit configured to measure a first base current generated by applying a predetermined potential to a sensor electrode when the sensor electrode is in contact with a reference solution before a first measuring process and a second base current generated by applying the predetermined potential to the sensor electrode when the sensor electrode is in contact with the reference solution after the first measuring process, a first peak current generated by applying the predetermined potential to the sensor electrode when the sensor electrode is in contact with the measured sample solution in the first measuring process and a second peak current generated by applying the predetermined potential to the sensor electrode when the sensor electrode is in contact with the measured sample solution in a second measuring process that is performed after the first measuring process;

a time counting unit configured to count an elapsed time from a time when the sensor electrode contacts the reference solution, where the biochemical measuring device is in a waiting state, until a time when the sensor electrode contacts the measured sample solution, where the biochemical measuring device is in a measurable state, wherein:

when the elapsed time is equal to or longer than a stabilization time, the measuring unit measures the concentration of the specific substance of the measured sample solution in the second measuring process using the second base current and the second peak current, and when the elapsed time is shorter than the stabilization time, the measuring unit measures the concentration of the specific substance of the measured sample solution in the second measuring process using the first base current and the second peak current, the stabilization time being a time required for a current value in measuring the base current value to return to a level of the stationary base current value after a previous measurement is conducted.

7. The biochemical measuring device according to claim 6, further comprising a notifying unit configured to remind a user when the second peak current is lower than the second base current when the elapsed time counted by the time counting unit is shorter than the stabilization time.

* * * * *